(12) United States Patent
Shimizu et al.

(10) Patent No.: US 6,673,583 B2
(45) Date of Patent: Jan. 6, 2004

(54) RECOMBINANTLY PRODUCING LEVODIONE REDUCTASE

(75) Inventors: Sakayu Shimizu, Kyoto (JP); Masaru Wada, San Diego, CA (US)

(73) Assignee: Roche Vitamins, Inc., Parsippany, NJ (US)

(*) Notice: Subject to any disclaimer, the term of this patent is extended or adjusted under 35 U.S.C. 154(b) by 0 days.

(21) Appl. No.: 10/327,726

(22) Filed: Dec. 23, 2002

(65) Prior Publication Data

US 2003/0138921 A1 Jul. 24, 2003

Related U.S. Application Data

(62) Division of application No. 09/773,748, filed on Jan. 31, 2001, now Pat. No. 6,534,297.

(30) Foreign Application Priority Data

Feb. 1, 2000 (EP) .............................................. 00101665

(51) Int. Cl.$^7$ ............................. C12P 7/24; C12N 9/02; C07H 21/04
(52) U.S. Cl. ....................... 435/148; 435/189; 536/23.2
(58) Field of Search ................................ 435/148, 189; 536/23.2

(56) References Cited

FOREIGN PATENT DOCUMENTS

| EP | 0 982 406 A2 | 3/2000 |
|---|---|---|
| EP | 1 026 235 A1 | 8/2000 |

OTHER PUBLICATIONS

Wada et al., "Purification and Characterization of Monovalent Cation–Activated Levodione Reductase from *Corynebacterium aquaticum* M–13," *Applied and Environmental Microbiology*, vol. 65, No. 10, pp. 4399–4403 (1999).

Database EMBL Online, Accession No. AB042262 of Wada, et al., "*Corynebacterium aquaticum* lvr gene for levodione reductase, complete cds," (May 2, 2000).

Ausubel et al., "Screening of Recombinant DNA Libraries," *Short Protocols in Molecular Biology*, New York: Greene Pub. Associates and Wiley–Interscience, Chapter 6.0.1–6.0.5 (1994).

Ausubel et al., "Construction of Hybrid DNA Molecules," *Short Protocols in Molecular Biology*, New York: Greene Pub. Associates and Wiley–Interscience, Chapter 3.16.1 (1995).

Ausubel et al., "Protein Expression," *Short Protocols in Molecular Biology*, New York: Greene Pub. Associates and Wiley–Interscience, Chapter 16.0.1–16.1.3 (2001).

Haugan et al., "Total Synthesis of Acetylenic Carotenoids," *Tetrahedron: Asymmetry*, vol. 5, No. 7, pp. 1367–1372 (1994).

Haugan et al., "Total Synthesis of $C_{31}$–Methyl Ketone Apocarotenoids," *Acta Chemica Scandinavica.*, vol. 51, pp. 1201–1216 (1997).

Pulido–Vega et al., "Transformation of Protoplasts of *Cellulomonas flavigena*," *Journal of Industrial Microbiology*, vol. 8, pp. 137–140 (1991).

Alemohammad and Pembroke, "Transformation of the Coryneform Bacterium *Cellulomonas Flavigena* With Plasmid DNA Via Electroporation," *Biotechnology Techniques*, vol. 4, No. 2, pp. 147–148 (1990).

Roberts et al., "Transformation of *Arthrobacter* and Studies on the Transcription of the *Arthrobacter ermA* gene in *Streptomyces lividans* and *Escherichia coli*," *Biochem. J.*, vol. 243, pp. 431–436 (1987).

*Primary Examiner*—Rebecca E. Prouty
*Assistant Examiner*—Sheridan L. Swope
(74) *Attorney, Agent, or Firm*—Bryan Cave LLP

(57) ABSTRACT

The present invention is directed to genetic material useful for the preparation of actinol, such as an isolated DNA including a nucleotide sequence coding for an enzyme having levodione reductase activity, a polypeptide encoded by such a DNA, recombinant organisms, and the like. These genetic materials may originate from Corynebacterium, Cellulomonas, Planococcus, Arthrobacter, and the like. The present invention also provides a process for the production of actinol.

9 Claims, No Drawings

RECOMBINANTLY PRODUCING LEVODIONE REDUCTASE

This application is a divisional of U.S. Ser. No. 09/773,748 filed Jan. 31, 2001, now U.S. Pat. No. 6,534,297, and claims priority thereto.

FIELD OF THE INVENTION

The present invention relates to DNA encoding levodione reductase, an expression vector containing the DNA, a recombinant vector containing the DNA, a microorganism into which the DNA has been introduced, and a method for producing (4R, 6R)-4-hydroxy-2,2,6-trimethylcyclohexanone (hereinafter referred to as actinol) from (6R)-2,2,6-trimethyl-1,4-cyclohexanedione (hereinafter referred to as levodione) using the microorganism. Actinol is a useful chiral building block of naturally occurring optically active compounds such as zeaxanthin.

BACKGROUND OF THE INVENTION

European Patent Application No. 98115564.1, filed on Aug. 19, 1998, discloses a process for the manufacture of actinol, which involves contacting levodione with a microorganism selected from the group consisting of microorganisms of the genera Cellulomonas, Corynebacterium, Planococcus and Arthrobacter, which is capable of selective asymmetric reduction of levodione to actinol, and recovering the resulting actinol from the reaction mixture. In this process, one of the most effective strains was *Corynebacterium aquaticum* AKU611 (FERM BP-6448), which was deposited with the National Institute of Bioscience and Human-Technology, Agency of Industrial Science and Technology, Japan, in the name of F. Hoffmann-La Roche A G of Grenzacherstrasse 124, CH-4070 Basel, Switzerland on Aug. 4, 1998, under the Budapest Treaty.

European Patent Application No. 99102037.1, filed on Feb. 1, 1999, discloses an enzyme, levodione reductase, that acts on levodione to produce actinol, which was isolated from *Corynebacterium aquaticum* AKU611 (FERM BP-6448). This enzyme is characterized by the following physico-chemical properties: 1) The levodione reductase catalyzes the regio- and stereoselective reduction of levodione to actinol. 2) The relative molecular mass of the enzyme is estimated to be 142,000–155,000±10,000 Da, consisting of four homologous subunits having a molecular mass of 36,000±5,000 Da. 3) The optimum temperature is 15–20° C. at pH 7.0 and the optimum pH is 7.5. 4) The enzyme requires $NAD^+$ or NADH as a cofactor and is highly activated by monovalent cations, such as $K^+$, $Na^+$, $Cs^+$, $Rb^+$, and $NH_4^+$.

SUMMARY OF THE INVENTION

An object of the present invention is a DNA sequence encoding for an enzyme, levodione reductase, which is useful for the preparation of actinol, an important intermediate in the production of zeaxanthin.

The isolated DNA sequence may be more specifically characterized by the following:
(a) the nucleotide sequence codes for the enzyme having the amino acid sequence shown in SEQ ID No.: 1, or
(b) the nucleotide sequence codes for a variant of the enzyme selected from (i) an allelic variant, or (ii) an enzyme having one or more amino acid additions, insertions, deletions and/or substitutions, but still having the same type of enzymatic activity.

The isolated DNA sequence mentioned above may be derived from a gene of *Corynebacterium aquaticum* and selected from
(i) the nucleotide sequence shown in SEQ ID No.: 2;
(ii) a nucleotide sequence which, because of the degeneracy of the genetic code, encodes a levodione reductase having the same amino acid sequence as that encoded by SEQ ID No: 2, or
(iii) a nucleotide sequence which hybridizes to the complement of the nucleotide sequence from (i) or (ii) under standard hybridizing conditions.

Another object of the present invention is a recombinant DNA which codes for levodione reductase and which can be obtained by genetic recombination of the isolated DNA described above. Such a recombinant DNA may preferably be in the form of a vector. The recombinant DNA may contain regulatory regions, such as promoters and terminators, as well as an open reading frame of the gene described above.

A further object of the invention is a recombinant organism consisting of a host organism transformed with the recombinant DNA. A preferred form of the recombinant DNA is a vector. The host organism transformed with the recombinant DNA may be useful in improving the process of actinol production.

Another object of the present invention is a method for the biological production of actinol that includes introducing a recombinant DNA, as described above, into an appropriate host organism, and cultivating the resulting recombinant organism in the presence of levodione as a substrate.

Accordingly, the invention provides an isolated polynucleotide encoding a polypeptide having levodione reductase activity.

Another embodiment of the invention is a vector or a plasmid containing a polynucleotide sequence encoding a polypeptide having levodione reductase activity wherein the polypeptide has the properties as set forth above.

A further embodiment of the invention is a microorganism transformed or transfected with a polynucleotide sequence which encodes a polypeptide having levodione reductase activity wherein the polypeptide has the properties as set forth above.

Another embodiment of the invention is an isolated polypeptide having levodione reductase activity wherein the polypeptide has the properties as set forth above.

A further embodiment of the invention is a process for producing a polypeptide having levodione reductase activity. This process includes culturing a microorganism transformed or transfected with a polynucleotide encoding a polypeptide having levodione reductase activity in nutrient media and isolating the polypeptide produced by the microorganism.

The present invention also provides a process for producing actinol. This process includes contacting levodione with a polypeptide having levodione reductase activity.

DETAILED DESCRIPTION OF THE INVENTION

As used herein, "levodione reductase" is a polypeptide that catalyzes, regio- and stereoselectively, the conversion of levodione to actinol in the presence of NADH. European Patent Application No. 99102037.1, filed on Feb. 1, 1999, discloses the physico-chemical properties of the levodione reductase. The levodione reductase of the invention can be prepared by cultivating an appropriate microorganism in an aqueous nutrient medium under aerobic conditions, disrupting the cells of the microorganism and isolating and purifying the levodione reductase from the cell-free extract. Many species have been found to catalyze this conversion, including the genera Cellulomonas, Corynebacterium, Planococcus and Arthrobacter. A preferred strain for the enzyme is *Corynebacterium aquaticum* AKU611 (FERM BP-6448).

As used herein, an "allele" or "allelic variant" is an alternative form of a gene, which may result from at least one mutation in the nucleic acid sequence. Alleles may result in altered mRNAs or polypeptides whose structure or function may or may not be altered. Any given gene may have none, one, or many allelic forms. Common mutational changes that give rise to alleles are generally ascribed to natural deletions, additions, or substitutions of nucleotides. Each of these types of changes may occur alone, or in combination with the others, one or more times, in a given sequence.

A "variant" of levodione reductase, as used herein, is an amino acid sequence that is altered by one or more amino acids. The variant may have "conservative" changes, wherein a substituted amino acid has similar structural or chemical properties, e.g., replacement of leucine with isoleucine. More rarely, a variant may have "non-conservative" changes, e.g., replacement of glycine with tryptophan. Similar minor variations may also include amino acid deletions or insertions, or both. A "deletion", as used herein, refers to a change in either the amino acid or nucleotide sequence in which one or more amino acid or nucleotide residues, respectively, are absent. An "insertion" or "addition", as used herein, refers to a change in an amino acid or nucleotide sequence resulting in the addition of one or more amino acid or nucleotide residues, respectively, as compared to the naturally occurring molecule. A "substitution", as used herein, refers to the replacement of one or more amino acids or nucleotides by different amino acids or nucleotides, respectively.

As used herein, "expression vector" includes vectors that are capable of expressing DNA sequences contained therein, where such sequences are operably linked to other sequences capable of effecting their expression. It is implied, although not explicitly stated, that expression vectors must be replicable in the host organisms either as episomes or as an integral part of chromosomal DNA. Clearly, a lack of replication would render them effectively inoperable. Thus, "expression vector" is also given a functional definition. Generally, expression vectors of utility in DNA recombinant techniques are in the form of "plasmids". "Plasmids" refer to either circular double stranded DNA molecules or circular single stranded DNA molecules, containing an origin of replication derived from a filamentous bacteriophage. These DNA molecules, in their vector form, are not linked to the chromosomes. Other effective vectors commonly used are phage and non-circular DNA. In the present specification, "plasmid" and "vector" are often used interchangeably. However, the invention is intended to include such other forms of expression vectors which serve equivalent functions and which are, or subsequently become, known.

"Recombinant host cells", "host cell", "cells", "cell cultures" and so forth, are used interchangeably herein to designate individual cells, cell lines, cell cultures, and harvested cells, which have been or are intended to be transformed with the recombinant vectors of the invention. The terms also include the progeny of the cells originally receiving the vector.

The terms "DNA," "nucleotide sequence" and "polynucleotide" or "polynucleotide sequence" are used interchangeably throughout and are intended to have the same meaning unless otherwise indicated. Likewise, the terms "amino acid sequence" and "polypeptide" are used interchangeably throughout and are intended to have the same meaning unless otherwise indicated.

"Transformed" or "transformation" refers to any process for altering the DNA content of the host.

As used herein, the phrase "standard hybridizing conditions" refers to conditions under which the person skilled in the art obtains a specific signal. The conditions may range from low stringency conditions (6×SSC, 50° C.; overnight; washing in 6×SSC at room temperature) to preferred medium stringency conditions (6×SSC; 65° C.; overnight; washing in 6×SSC at 30° C.) to the most preferred high stringency conditions (6×SSC; 75° C.; overnight; washing two times in 6×SSC at 37° C.). Alternatively, the degree of similarity can be determined by the percentage of homology. For the determination of homology the two sequences to be compared are aligned to each other by a suitable computer program. Using the standard conditions of the program, the claimed sequences have a percentage of homology of at least 40%, preferably, at least 60%, and more preferable at least 80%, with the sequences disclosed in the present application.

Amino acids are identified by either their single-letter or three-letter designations:

| AMINO ACID ABBREVIATIONS | |
|---|---|
| A = Ala = Alanine | V = Val = Valine |
| L = Leu = Leucine | I = Ile = Isoleucine |
| P = Pro = Proline | F = Phe = Phenylalanine |
| W = Trp = Tryptophan | M = Met = Methionine |
| G = Gly = Glycine | S = Ser = Serine |
| T = Thr = Threonine | C = Cys = Cysteine |
| Y = Tyr = Tyrosine | N = Asn = Asparagine |
| Q = Gln = Glutamine | D = Asp = Aspartic Acid |
| E = Glu = Glutamic Acid | K = Lys = Lysine |
| R = Arg = Arginine | H = His = Histidine |

The following is a list of commercial suppliers for materials used in this invention:

a. Invitrogen: 1600 Faraday Avenue, Carlsbad, Calif. 92008, USA
b. Amersham Pharmacia Biotech: SE-751 84 Uppsala, Sweden
c. Toyobo: 2-2-8 Dojimahama, Kita-ku, Osaka, Japan
d. Takara Shuzo: 2-15-10 Nihonbashi, Chuo-ku, Tokyo, Japan
e. Promega: 2800 Woods Hollow Road, Madison, Wis., USA
f. BIO101: 2251 Rutherford Rd., Carlsbad, Calif. 92008, USA
g. PE Biosystems: 850 Lincoln Center Drive, Foster City, Calif. 94404, USA
h. Shimadzu: 1 Nishinokyo, Kuwabaracho, Nakagyo-ku, Kyoto, Japan
i. Shinwa Chemical Industries: 50 Keishocho, Fushimi-ku, Kyoto, Japan
j. Wako Pure Chemicals: 3-1-2 Doshoumachi, Chuo-ku, Osaka, Japan
k. Oriental Yeast: 3-6-10 Shodosawa, Itabashi-ku, Tokyo, Japan
l. Amano Pharmaceuticals: 1-2-7 Nishiki, Naka-ku, Nagoya, Japan The gene encoding levodione reductase is a DNA encoding a polypeptide having the enzyme activity of converting levodione to actinol. A typical example of this gene is a levodione reductase gene which can be cloned from *Corynebacterium aquaticum* AKU611 (FERM BP-6448). This DNA contains a nucleotide sequence coding for a polypeptide containing the amino acid sequence as shown in SEQ ID No.: 1.

The DNA sequence may be cloned from a strain of *Corynebacterium aquaticum* AKU611 (FERM BP-6448), or another related organism and thus, may be an allelic or species variant of the levodione reductase encoding region of the DNA sequence. Also included within the scope of the present invention is a derivative of the DNA sequence with additions, insertions, deletions and/or substitutions of different nucleotides resulting in a polypeptide that encodes the same or a functionally equivalent levodione reductase. For example, the derivative may contain from 1–100, preferably 1–50, more preferably 1–10 to 1–5 additions, insertions, deletions and/or substitution of nucleotides, so long as the derivative encodes a polypeptide have levodione reductase activity. The encoded protein may also contain addition, deletions, insertions and/or substitutions of amino acid residues that produce a silent change and result in a functionally equivalent levodione reductase. For example, the derivative protein may contain from 1–100, preferably 1–50, more preferably 1–10 to 1–5 additions, insertions, deletions and/or substitution of amino acids so long as the derivative still retains its function (i.e., levodione reductase activity).

The levodione reductase gene product, i.e. the levodione reductase of the present invention, has, as described above, an enzyme activity to convert levodione to actinol. The gene for such an enzyme activity has not been previously described. However, by using the levodione reductase gene, it is possible to confer on a microorganism, such as E. coli, the ability to convert levodione to actinol.

The present invention provides an isolated DNA sequence that codes for an enzyme, levodione reductase, which is involved in the conversion of levodione to actinol. The DNA can include genomic DNA which contains regulatory sequences such as promoters and terminators that are involved in the expression of the gene of interest, and a cDNA which contains an open reading frame flanked between short fragments in its 5'- and 3'-untranslated region.

The levodione reductase gene, the recombinant expression vector, and the recombinant organisms utilized in the present invention may be obtained by the following; steps:

(1) Isolating chromosomal DNA from a microorganism that can provide the levodione reductase of the present invention and constructing a gene library with the chromosomal DNA.

(2) Cloning the levodione reductase gene from chromosomal DNA by colony- or plaque-hybridization, PCR cloning, Southern-blot hybridization, and the like.

(3) Determining the nucleotide sequence of the levodione reductase gene by conventional methods, and constructing recombinant expression vectors that contain and efficiently express the levodione reductase gene.

(4) Constructing recombinant organisms carrying the levodione reductase gene on recombinant expression vectors or in chromosomes by transformation, transduction, transconjugation and electroporation.

The techniques used to isolate or clone DNA encoding the levodione reductase of the present invention are known in the art and include the isolation from genomic DNA. The cloning of the DNA sequence of the present invention from genomic DNA can be effected, for example, using degenerate polymerase chain reaction (PCR).

To clone the levodione reductase gene, knowledge of the amino acid sequence of levodione reductase may be necessary. Levodione reductase protein may be purified and a partial amino acid sequence may be determined by conventional methods (Biosci. Biotechnol. Biochem. 62, 280–285, (1998)). Determination of the complete amino acid sequence is not necessary. Once suitable amino acid sequences have been identified, oligonucleotides for use as PCR primers are synthesized on the basis of information on the partial amino acid sequences. The primers used for cloning the levodione reductase gene by PCR are based on the amino acid sequence of the internal peptide fragments of the purified levodione reductase from the genera including, for example, Corynebacterium, Cellulomonas, Planococcus and Arthrobacter, and in the most preferred embodiment, from *Corynebacterium aquaticum* AKU611 (FERM BP-6448). A DNA fragment (i.e., a partial DNA sequence) for levodione reductase is generated by PCR amplification using the primers and a template of *Corynebacterium aquaticum* chromosomal DNA. The amplified DNA fragment can then be used as a probe to clone a genomic fragment coding for the whole levodione reductase of *Corynebacterium aquaticum* AKU611 (FERM BP-6448).

An entire gene containing its coding region as well as its regulation region, such as a promoter or terminator, can be cloned from a chromosome by screening a genomic library with a labeled probe. The genomic library should be constructed in phage or plasmid vectors in an appropriate host. The probe used to screen the library should be a partial DNA fragment obtained by PCR, as described above, that has been labeled. Generally, an E. coli vector, a phage vector (e.g., λ phage vector), a plasmid vector, or a yeast vector, and E. coli as a host strain, are used in the construction of a library and for subsequent genetic manipulations, such as a sequencing, restriction digestion, ligation, and the like. Identification of desired clones from the plasmid or phage library is best effected by selecting a probe, such that the desired gene will hybridize to the probe under high stringency conditions.

A genomic library of *Corynebacterium aquaticum* AKU611 (FERM BP-6448) was constructed in pYES2. The PCR-amplified fragment used as a probe was labeled with horseradish peroxidase ("HRP"), according to the supplier's protocol (Amersham Pharmacia Biotech), instead of a conventional $^{32}P$ labeling method. A genomic library constructed from the chromosome of *Corynebacterium aquaticum* AKU611 (FERM BP-6448) was screened with an HRP-labeled DNA fragment, which had a portion of the gene of interest, as a probe. Hybridized colonies were picked up and used for further study. After the isolation of positive colonies, the insert fragments were subcloned into an appropriate sequencing vector. The insert fragments were then subcloned into a pUC18 vector.

The nucleotide sequence of the target gene can be determined by a well-known sequencing method such as the dideoxy chain-termination method (Proc. Natl. Acad. Sci. USA, 74, 5463–5467, (1977)).

The isolated DNA sequence of the present invention may also be used to identify and clone DNA encoding a polypeptide having levodione reductase activity from other strains of different genera or species according to methods well known in the art.

The present invention also includes a recombinant DNA, preferably a vector and/or plasmid, containing a sequence coding for levodione reductase. The recombinant DNA vector and/or plasmid may contain the regulatory regions, such as promoters and terminators, as well as open reading frames of the above mentioned DNA.

Methods which are well known to those skilled in the art may be used to construct expression vectors containing a sequence encoding levodione reductase and appropriate transcriptional and translational regulatory elements, including all components which are necessary or advantageous for expression of the coding sequence as described in Ausubel F. M. et al., Current Protocols in Molecular Biology, John Wiley & Sons, New York, N.Y. (1989). Specific initiation and termination signals, may also be used to achieve more efficient translation of sequences encoding levodione reductase.

An isolated DNA sequence encoding levodione reductase may be manipulated in a variety of ways to provide for expression of the polypeptide. Manipulation of the nucleotide sequence encoding the levodione reductase prior to its insertion into a vector may be desirable, or necessary, depending on the expression vector. The techniques for modifying nucleotide sequences utilizing cloning methods are well known in the art.

A variety of expression vector/host systems may be utilized to contain and express sequences encoding levodione reductase. These systems include, for example, microorganisms, such as bacteria, transformed with recombinant bacteriophage, plasmid, or cosmid DNA expression vectors; yeast transformed with yeast expression vectors; plant cell systems transformed with viral expression vectors or with bacterial expression vectors; or animal cells. An expression vector is selected according to the use intended for the levodione reductase. For example, when large quantities of levodione reductase are needed, vectors that direct high level expression of the introduced DNA sequence may be used. Such vectors include, for example, the E. coli cloning and expression vectors, such as pBluescript II and pUC18.

The host cell, which is transformed with the DNA sequence coding for levodione reductase, may be either eukaryotic or prokaryotic. The choice of a host cell may, to a large extent, depend on the gene encoding the polypeptide and that gene's source. Suitable prokaryotic host cells include bacterial cells, such as E. coli, which are used to provide for the high level expression of protein. In order to overexpress an enzyme of interest, promoter systems suitable for high level expression may be used. Such promoters include, for example, the lac or T7 expression systems.

The present recombinant DNAs, vectors, or plasmids may be used to transform a host organism. The recombinant organism obtained is capable of overexpressing the DNA sequence encoding levodione reductase. Thus, the host organism transformed with the recombinant DNA is useful in the production process of actinol. Accordingly, the present invention also includes recombinant organisms and transformed host cells.

A method for producing levodione reductase is also provided. This method includes culturing the recombinant organism of the present invention under conditions conducive to the production of the enzyme. Host cells transformed with nucleotide sequences encoding levodione reductase may be cultured under conditions suitable for the expression and recovery of the protein from a cell culture.

The recombinant organism of the present invention may be cultured in nutrient medium containing saccharides, such as glucose and sucrose, alcohols, such as ethanol and glycerol, fatty acids, such as oleic acid and stearic acid or esters thereof, or oils, such as rapeseed oil and soybean oil, as carbon sources; ammonium sulfate, sodium nitrate, peptone, amino acids, corn steep liquor, bran, yeast extract, and the like, as nitrogen sources; magnesium sulfate, sodium chloride, calcium carbonate, potassium monohydrogen phosphate, potassium dihydrogen phosphate, and the like, as inorganic salt sources; and malt extract, meat extract, and the like, as other nutrient sources. Cultivation of the recombinant organism can be carried out aerobically or anaerobically, preferably for a period of 1 to 7 days at a medium pH of 3 to 9 and a cultivation temperature of 10 to 40° C.

The levodione reductase produced by a recombinant cell of the present invention may be secreted or contained intracellularly depending on the sequence and/or the vector used. The levodione reductase may then be isolated from the culture medium, or the host cell, by conventional procedures.

The present invention also provides a process for the isolation and purification of levodione reductase from the recombinant cells after cultivation as follows:

(1) Cells are harvested from the liquid culture broth by centrifugation or filtration.
(2) The harvested cells are washed with water, physiological saline, or a buffer having an appropriate pH.
(3) The washed cells are suspended in the buffer solution and disrupted by means of a homogenizer, sonicator, French press, or treatment with lysozyme, and the like, to give a solution of disrupted cells.
(4) The levodione reductase is isolated and purified from the cell-free extract of disrupted cells.

Following confirmation of enzyme activity, the expressed levodione reductase protein may be used for raising antibodies to the purified enzyme. The antibody may then be used for characterizing the expression of the corresponding enzyme in a strain improvement study, an optimization study of culture conditions, and the like.

The following examples are provided to further illustrate methods of preparation of the compositions of the present invention, as well as certain physical properties and uses thereof. These examples are illustrative only and are not intended to limit the scope of the invention in any way.

The following materials and methods were employed in the Examples described below. All % are % (wt) unless otherwise noted.

Strains

*Corynebacterium aquaticum* AKU611 (FERM BP-6448)

*E. coli* DH5α: [φ80δlacZΔM15, F$^-$, λ$^-$, Δ(lacZYA-argFV169), hsd R17($r_K^-$, $m_K^+$), recA1, endA1, supE44, deoR, thi-1, gyrA96, relA1] (Toyobo, Osaka, Japan).

*E. coli* JM109: [recA1, endA1, gyrA96, thi, hsdR17($r_K^-$, $m_K^+$), mcrB$^+$, supE44, relA1, Δ(lac-proAB), F'(traD36, proAB, lacI$^q$, lacZΔM15), λ$^-$] (Toyobo, Osaka, Japan).

Vectors
pYES2 (Invitrogen)
pGEM-T (Promega)
pUC18 (Toyobo)

| Primers | |
|---|---|
| T-7 primer: | 5'-TAATACGACTCACTATAGGG-3' |
| SP6 primer: | 5'-TACGATTTAGGTGACACTAT-3' |
| M13 primer M4: | 5'-GTTTTCCCAGTCACGAC-3' |
| M13 primer RV: | 5'-CAGGAAACAGCTATGAC-3' |

Media

*Corynebacterium aquaticum* AKU611 (FERM BP-6448) was cultured aerobically at 30° C. for 20 hours in a medium (pH 7.0) containing 1% glucose, 1.5% peptone, 0.3% $K_2HPO_4$, 0.1% yeast extract, 0.2% NaCl, and 0.02% $MgSO_4$ $7H_2O$. *E. coli* transformants containing the *Corynebacterium aquaticum* AKU611 (FERM BP-6448) levodione reductase gene were grown in Luria-Bertani medium (LB medium) consisting of 10 g of tryptone, 10 g of sodium chloride, and 5 g of yeast extract (pH 7.2)/liter, or in M9 medium (page A-3, Molecular Cloning, 1989, Cold Spring Harbor Laboratory Press) supplemented with casamino acids.

Enzymes and Chemicals

Restriction endonucleases and other DNA-modifying enzymes were obtained from Takara Shuzo and Toyobo. Ex taq, a Taq DNA polymerase, and Ex taq buffer were purchased from Takara Shuzo. ECL direct nucleic acid labeling and detection systems were purchased from Amersham Pharmacia Biotech.

Methods

General methods of molecular genetics were practiced according to Molecular Cloning: A Laboratory Manual, 2nd Edition, Cold Spring Harbor Laboratory Press (1989).

Chromosomal DNA from *Corynebacterium aquaticum* AKU611 (FERM BP-6448) was isolated using a Genome Isolation Kit (BIO101).

Polymerase chain reaction (PCR) was performed with a thermal cycler (PE Biosystems). Degenerate PCR primers were synthesized by the phosphoramidite method using an Applied Biosystems Model 381A automatic synthesizer (PE Biosystems).

Nucleotide sequence analysis was performed using the dideoxy chain-termination method (Proc. Natl. Acad. Sci. USA, 74, 5463–5467 (1977)). A Taq dye primer sequencing kit was used with an autosequencer (DNA Sequencer 377A, PE Biosystems).

Levodione reductase activity was determined by spectrophotometrically measuring the levodione-dependent decrease in the absorbance of NADH content at 340 nm. A standard 2.5 ml assay mixture contained 5 μmole of levodione (final concentration, 2.0 mM), 0.8 μmole of NADH, 500 μmole of potassium phosphate buffer (pH 7.0), and the enzyme. One unit of the enzyme activity was defined as the amount of enzyme that catalyzes oxidation of 1 μmole of NADH per minute.

Quantitative analysis of the levodione and actinol content was performed with a Shimadzu model GC-14B GC equipped with a flame ionization detector using a type HR-20M capillary column (0.25 mm by 30 m; Shinwa Chemical Industries) at 160° C. (isothermal) and He as the carrier gas at a flow rate of 1 ml/min. Under these conditions, levodione, actinol, and (4S,6R)-hydroxy-2,2,6-trimethylcyclohexanone (a diastereomer of actinol) eluted at 6.8, 15.6, and 15.9 minutes, respectively.

Purification of levodione reductase was performed according to the procedures disclosed in European Patent Application No. 99102037.1 filed on Feb. 1, 1999, and included the use of any of the following, alone or in combination: fractionation with precipitants (e.g., ammonium sulfate, polyethylene glycol and the like), ion exchange chromatography, absorption chromatography, gel-filtration chromatography, gel electrophoresis, and salting out and dialysis. The purified enzyme was digested with lysyl endopeptidase (Wako Pure Chemicals) under the conditions described in Appl. Environ. Microbiol. 62, 2303–2310, 1996. The peptides were separated by reverse-phase high-performance liquid chromatography on a μRPC C2/C18 column (Amersham Pharmacia Biotech) connected to a Smart system (microscale protein purification system; Amersham Pharmacia Biotech). The peptides were eluted with a linear 0 to 80% acetonitrile gradient containing 0.1% trifluoroacetic acid.

A partial amino acid sequence was determined by automated Edman degradation with a model 476A pulsed liquid protein sequencer (PE Biosystems) as described previously (Biosci. Biotechnol. Biochem. 62, 280–285, 1998). The partial amino acid sequence obtained was compared with the sequences of proteins stored in the SWISS-PROT (release 37.0+/06-June 14, 1999), PIR (release 60.0, March 1999), and PRF (release 99-May 5, 99) protein databases. Sequence alignment was performed by using the Blast (J. Mol. Biol. 215, 403–410, 1990) and Fasta (Proc. Natl. Acad. Sci. USA 85, 2444–2448, 1988) programs.

EXAMPLE 1

Partial Amino Acid Sequence from *Corynebacterium aquaticum* AKU611 (FERM BP-6448)

The N-terminal amino acid sequence of purified *Corynebacterium aquaticum* levodione reductase was determined by automated Edman degradation using a model 476A pulsed liquid protein sequencer (PE Biosystems). The sequence is similar to the $NH_2$-terminal amino acid sequences of other short-chain dehydrogenase/reductase (SDR) family enzymes, such as the biphenyl-2,3-dihydro-2,3-diol dehydrogenase of Pseudomonas sp. strain KKS102 (Biochem. Biophys. Res. Commun. 2.02, 850–856, 1994). Moreover, this $NH_2$-terminal amino acid sequence contains G-X-X-X-G-X-G, which is a highly conserved motif in the $NH_2$-terminal regions of SDR family proteins. The amino acid sequence obtained from the N-terminal of levodione reductase is shown in Table 1.

TABLE 1

N-terminal amino acid sequence (SEQ ID NO:3)
TATSSPTTRFTDRVVLITGGGSGLGRATAVRLAAEGAKLSSVD The levodione reductase protein was digested with lysyl endopeptidase, and the resulting digest was separated by the Smart system (Amersham Pharmacia Biotech). The K-1, K-2, and K-3 peptides were isolated, and the amino acid sequences of these peptides were analyzed with a protein sequencer. The K-1, K-2, and K-3 sequences are shown in Table 2. When these sequences were compared with the sequences in three protein sequence databases (PIR, PRF, and SWISS-PROT) using the sequence similarity search programs Blast and Fasta, the K-1 and K-2 sequences were found to be significantly similar to partial amino acid sequences of a 2,5-dichloro-2,5-cyclohexadiene-1,4-diol dehydrogenase of *S. paucimobilis* (J. Bacteriol. 176, 3117–3125, 1994) and a 3-oxoacyl-[acyl-carrier protein] reductase of *Haemophilus influenzae* (Whole-genome random sequencing and assembly of *Haemophilus influenzae* Rd, Science 269, 495–512, (1995)), respectively, both of which belong to the SDR family. However, K-3 did not exhibit significant similarity to any other SDR family proteins.

TABLE 2

Partial amino acid sequences of K-1, K-2, and K-3

Peptide K-1:
HGVVGLTRNSAVEYGRYGIRINAIA          (SEQ ID NO:4)

Peptide K-2:
RYGEAPEIAAVVAFLLSDDASYVNA          (SEQ ID NO:5)

Peptide K-3:
AAVLETAPDAEVLTT                    (SEQ ID NO:6)

EXAMPLE 2

Construction of a Genomic DNA Library

Chromosomal DNA from *Corynebacterium aquaticum* AKU611 (FERM BP-6448) was prepared using a Genome Isolation Kit (BIO101). The chromosomal DNA was partially digested with Sau3AI. The digested chromosomal DNA was then fractionated by agarose gel electrophoresis. DNA fragments (500 ng) of predominantly 2–3 kb in size were mixed with BamH1-digested pYES2 vector (200 ng), and ligated using Ligation High (Toyobo) at 16° C. for 30,minutes in vitro. The ligation mixture was then used to transform competent *E. coli* DH5α cells (Toyobo). Transformed *E. coli* DH5α cells were plated and cultured on LB agar plates containing ampicillin at 37° C. overnight. A genomic library (2,242 colonies) was thus obtained.

EXAMPLE 3

The Cloning of Levodione Reductase Genomic DNA by PCR Amplification and the Amplification of a Partial Levodione Reductase Gene of *Corynebacterium aquaticum* AKU611 (FERM BP-6448)

Degenerate oligonucleotide primers were designed and synthesized based on the amino acid sequences of the internal peptide fragments (Table 2) of the levodione reductase from *Corynebacterium aquaticum* AKU611 (FERM BP-6448). The primers, 2–23(+) and 2–23(−) were synthesized on the basis of the amino acid sequence, YGEAPEI, of peptide K-2, and the primers, 1–19(+) and 1–19(−), on the basis of the amino acid sequence, AVEYGRY, of peptide K-1, as shown in Table 3. The primers, 1–19(+) and 1–19(−), each contained one inosine moiety.

TABLE 3

Sequence of primers used to clone the levodione reductase gene

| | | |
|---|---|---|
| 2-23(+): | 5'-TAYGGNGARGCNCCNGARAT-3' | (SEQ ID NO:7) |
| 2-23(−): | 5'-ATYTCNGGNGCYTCNCCRTA-3' | (SEQ ID NO:8) |
| 1-19(+): | 5'-GCNGTNGARTAYGGNMGITA-3' | (SEQ ID NO:9) |
| 1-19(−): | 5'-TAICKNCCRTAYTCNACNGC-3' | (SEQ ID NO:10) |

(R = A or G, K = G or T, Y = C or T, M = A or C, N = A, C, G or T)

Genomic DNA was amplified by PCR using a thermal cycler (PE Biosystems). The PCR reactions (20 μl) were carried out using 100 ng of *Corynebacterium aquaticum* AKU611 (FERM BP-6448) chromosomal DNA as a template, 5 μM of each degenerate primer, 312 μM each of dATP, dCTP, dGTP, and dTTP, 2.5 U (final concentration) of Ex Taq (Takara Shuzo) as a DNA polymerase, and 2 μl of EX Taq buffer (Takara Shuzo). Taq polymerase (2.5 U) was added after the reaction had been incubated at 95° C. for 5 minutes. The reaction was then cycled 25 times as follows: 95° C. for 30 seconds, 42° C. for 30 seconds, and 72° C. for 2 minutes. Various combinations of primers were tested and one combination (2–23(−) and 1–19(+)) resulted in a prominent band. The reaction products were isolated and purified using agarose gel electrophoresis. An adenine tail was added to the gel-purified PCR product at the 3'-terminal ends, and ligated into a pGEM-T vector. The ligation mixture was used to transform competent *E. coli* DH5α. After the cultivation of transformants, plasmid DNA was extracted. The nucleotide sequence was then determined by an autosequencer using the T-7 and SP6 primers that are derived from the T vector. Sequencing results indicated that the PCR product was composed of 172 nucleotide base pairs (Table 4). The deduced amino acid sequence was consistent with the internal amino acid sequence of the native levodione reductase protein.

TABLE 4

DNA and deduced amino acid sequences of the PCR amplified fragment (SEQ ID NO:11)
```
        10        20        30        40
GCAGTCGAGTATGGGCGGTACGGCATCCGCATCAACGCCATCGCCCCC
  A  V  E  Y  G  R  Y  G  I  R  I  N  A  I  A  P 50        60        70        80        90
GGCGCCATCTGGACGCCGATGGTCGAGAACTCGATGAAGCAGCTCGAC
  G  A  I  W  T  P  M  V  E  N  S  M  K  Q  L  D 100       110       120       130       140
CCGGAGAACCCCCGCAAGGCCGCCGAGGAGTTCATCCAGGTCAACCCC
  P  E  N  P  R  K  A  A  E  E  F  I  Q  V  N  P 150       160       170
TCCAAGCGCTACGGCGAAGCCCCAGAGA
  S  K  R  Y  G  E  A  P  E
```

EXAMPLE 4

Cloning of the Levodione Reductase Gene from *Corynebacterium aquaticum* AKU611 (FERM BP-6448)

(1) Cloning of the Levodione Reductase Genomic Gene from *Corynebacterium aquaticum* AKU611 (FERM BP-6448) using the PCR Amplified Product as a Probe The PCR amplified 172-bp fragment was used to isolate the levodione reductase gene from the genomic DNA library. The PCR amplified 172-bp fragment was denatured by heat treatment and labeled with horseradish peroxidase (HRP) using the ECL direct nucleic acid labeling and detection system (Amersham Pharmacia Biotech), according to the manufacturer's instructions. The library (2,242 colonies), as described in Example 2, was transferred onto Hybond N+, a positively charged nylon membrane (Amersham Pharmacia Biotech), and then denatured and fixed with buffer containing 0.5 M NaOH. The membranes were then probed with the HRP-labeled PCR fragment. After hybridization, the membranes were washed and the positive clones on the membranes were detected using a chemiluminescent detection system. From 2,242 colonies (recombinants) in the genomic library, twenty-five positive clones were obtained.

To investigate whether gene fragments of the levodione reductase were contained in these clones, and to select positive clones, PCR was performed with the 1–19(+) and 2–23(−) primers, and each one of the twenty-five clones as a template. The reaction mixture (20 μl) contained 0.5 μM of each primer, 10 ng of a template (each one of the 25 clones), 312 μM of each dNTP, 2.5 U (final concentration) EX Taq (Takara Shuzo) as a DNA polymerase, and 2 μl of EX Taq buffer (Takara Shuzo). PCR conditions used were: 96° C. for 1 minute followed by 25 cycles at 95° C. for 30 seconds, 55° C. for 30 seconds, and 72° C. for 1 minute. As a result, clone No. 27, carrying an approximately 8.5 kb DNA fragment, which contained about 2.7 kb of insert DNA, was selected for further analysis.

(2) Nucleotide Sequencing of Clone No. 27

DNA sequencing was performed with an autosequencer using the primer walking technique. The pYES2(+) and pYES2(−) primers, derived from pYES2, and the 2–23(−), 27–2(−), and 27–1(−) primers, derived from the internal peptide fragments, were used for DNA sequencing. About 260 bp from the pYES2(+) side, and about 820 bp from the pYES2(−) side, were sequenced. The sequences of the primers used are shown in Table 5.

TABLE 5

Sequence of the primers pYES2(+):
5'-GCCAGTGTGATGGATATCTGCAG-3'    (SEQ ID NO:12)

pYES2(−):
5'-GGATCGGACTACTAGCAGCTG-3'    (SEQ ID NO:13)

27-2(−):
5'-TAATCGGTCATGCACCCGTGTC-3'    (SEQ ID NO:14)

27-1(−):
5'-AGACCGAGCTGGTCGAGGCTCT-3'    (SEQ ID NO:15)

To analyze the nucleotide sequence in more detail, clone No. 27 was digested with Sac I for subcloning and DNA sequencing. Two fragments with sizes of 7.5 kb and 1 kb were isolated and purified using agarose gel electrophoresis. The 7.5 kb fragment, including 1.6 kb of insert DNA, was circularized by self-ligation using Ligation High, and the 1 kb fragment was ligated with Sac I-digested pUC18 vector using Ligation High (Toyobo). Each ligation mixture was used to transform *E. coli* JM109 cells. The *E. coli* JM109 cells were then placed and cultured on LB agar plates at 37° C. overnight. The nucleotide sequence of each transformant obtained was determined by an autosequencer.

(3) Nucleotide Sequencing of the 1 kb Fragment

The nucleotide sequence of the 1 kb fragment was determined using the M4 and RV primers for M13 vectors, and the SUB27(+) primer derived from the sequence of this fragment. The sequence of the SUB27 primer is shown in Table 6.

TABLE 6

Sequence of the SUB2 7 primer

SUB27(+):
5'-ACTACCAGAACAGCATCGTCGA-3'    (SEQ ID NO:16)

The nucleotide sequence of the 1 kb fragment was consistent with that of the pYES2(−) side of clone No. 27. A portion (441 bp) of the deduced Open Reading Frame ("ORF") was present in this fragment.

(4) Nucleotide Sequence of the 7.5 kb Fragment

DNA sequencing of the 1.6 kb insert DNA in the 7.5 kb fragment was performed using the pYES2(+) and pYES2 (−), primers for pYES2, and the P-2(+), P-3(+), P-4(+), SUB No.1(−), SUB No.2(−), SUB No.3(−), P-4(−), and P-3(−), primers derived from the sequence of this fragment. The sequences of the primers used are shown in Table 7.

TABLE 7

Sequence of the primers

P-2(+):
5'-TTCATCGAGTTCTCGACCATCG-3'    (SEQ ID NO:17)

P-3(+):
5'-TGAACGACTCGGTCGGGTTCTG-3'    (SEQ ID NO:18)

P-4(+):
5'-AGACGTCGACGAGGGAGAGCTT-3'    (SEQ ID NO:19)

TABLE 7-continued

Sequence of the primers

SUB No.1(−):
5'-TCACGTCCGTCCTCGTCGTCCT-3'    (SEQ ID NO:20)

SUB No.2(−):
5'-TGACTTCGGCACCGCGTGGCTC-3'    (SEQ ID NO:21)

SUB No.3(−):
5'-AAGTCGTTCCGGTGCACGTACA-3'    (SEQ ID NO:22)

P-4(−):
5'-CTCCCCATGACCGCAACCAGCT-3'    (SEQ ID NO:23)

P-3(−):
5'-CAGAACCCGACCGAGTCGTTCA-3'    (SEQ ID NO:24)

Nucleotide sequence analysis of the 1.6 kb insert DNA revealed that it contained 708 bp of the levodione reductase gene lacking its C-terminal region. It was found that the nucleotide sequence of this fragment contained nucleotides of the internal peptide (F27), the N-terminus, and the first methionine (Met). The presence of a Shine-Delgarno (SD) sequence upstream of the first Met was also indicated. To clone the full-length ORF, the 708 bp fragment was used to design a probe.

(5) Construction of a Genomic Library and Screening of the Full Length Levodione Reductase Gene with the 708-kb Fragment as a Probe Chromosomal DNA from *Corynebacterium aquaticum* AKU611 (FERM BP-6448) was prepared using a Genome Isolation Kit (BIO101). The chromosomal DNA was partially digested with Sac I. The digested chromosomal DNA was then fractionated by agarose gel electrophoresis. DNA fragments (500 ng) of predominantly 4 kb in size were mixed with Sac I-digested pYES2 vector (200 ng), and ligated using Ligation High (Toyobo) at 16° C. for 30 minutes in vitro. The ligation mixture was used to transform competent *E. coli* DH5α cells (Toyobo). Transformed *E. coli* DH5α cells were plated and cultured on LB agar plates containing ampicillin at 37° C. overnight. A genomic library (974 colonies) was thus obtained. The 708-bp fragment obtained in Example 4 (4) was used to screen for the levodione reductase gene in the genomic DNA library. The 708-bp fragment was denatured by heat treatment and labeled with HRP using the ECL direct nucleic acid labeling and detection system (Amersham Pharmacia Biotech) according to the manufacturer's instructions. The library (974 colonies) was transferred onto Hybond N+, a positively charged nylon membrane (Amersham Japan), and then denatured and fixed with buffer containing 0.5 M NaOH. The membranes were then probed with the HRP-labeled PCR fragment. After hybridization, the membranes were washed and positive clones on the membranes were detected using a chemiluminescent detection system. From 974 colonies (recombinants) in the genomic library, fifty positive clones were obtained.

To further select a positive clone, PCR was performed using pYES2(+), pYES2(−), 2–23(−), and the first Met(+) as primers, and each one of the fifty positive clones as a template. The reaction mixture (20 μl) contained 0.5 μM of each primer, 10 ng of a template (each one of the 50 positive clones), 312 μM of each dNTP, 2.5 U (final concentration) EX Taq (Takara Shuzo) as a DNA polymerase, and 2 μl of EX Taq buffer (Takara Shuzo). PCR conditions used were 95° C. for 1 minute followed by 25 cycles at 95° C. for 30 seconds, 55° C. for 30 seconds, and 72° C. for 1 minute. As a result, one positive clone, containing a 3 kb DNA insert, was selected for sequencing.

DNA sequencing of the isolated clone was performed using P-3(−) and P-2-2(−) as primers. The sequence of primer P-2-2(−) is shown in Table 8.

TABLE 8

Sequence of primer P-2-2(−)

P-2-2(−):
5'-GAACTCGATGAAGCAGCTCGAC-3'    (SEQ ID NO:25)

DNA sequence analysis of this clone revealed a levodione reductase gene region of 804 bp encoding a protein of 267 amino acids (SEQ ID No.: 1). The stop codon, TGA, was present approximately 100 bp downstream of the probe sequence. The molecular mass (27.9 KDa) of levodione reductase was calculated by DNASIS.

The deduced amino acid sequence was compared with other protein sequences. A high level of identity was found with the 2,5-DDOL-dehydrogenase (Lin C) of *Sphingomonas paucimobilis* UT26 (37%).

EXAMPLE 5

Expression of the Levodione Reductase Gene, and Production of Actinol from Levodione in *E. coli*.
(1) Construction of a Recombinant DNA Harboring the levodione reductase gene Chromosomal DNA from *Corynebacterium aquaticum* AKU611 (FERM BP-6448) was prepared using a Genome Isolation Kit (BIO101). Oligonucleotide primers were designed and synthesized based on the amino acid sequences of the upstream N-terminal, and the downstream C-terminal, regions of the levodione reductase gene, as shown in Table 9. EcoRI sites were constructed in both primers to obtain the levodione reductase gene in an EcoRI fragment for use in constructing an expression vector.

TABLE 9

Sequence of the designed primers for the upstream and the downstream regions of the levodione reductase gene Upstream primer:    5'-CACGACGAATTCGCGCGGATCCTGCGGACCTGC-3'    (SEQ ID NO:26)

Downstream primer: 5'-CCGTGACTTAAGCAGCCATGTCCGCAGCCT-3'    (SEQ ID NO:27)

The target DNA fragment was amplified using a thermal cycler (PE Biosystems). The PCR reactions (20 µl) were carried out using 5 ng of plasmid DNA including the full length levodione reductase gene as a template, 250 nmole of each of the primers, 0.2 mM each of dATP, dCTP, dGTP, and dTTP, 1 U (final concentration) of Ex Taq (Takara Shuzo) as a DNA polymerase, and 2 µl of Ex Taq buffer (Takara Shuzo). After the reaction mixture was incubated at 94° C. for 1 minute, the reaction was then cycled 25 times as follows: 98° C. for 20 seconds, 70° C. for 2 minutes, and 72° C. for 4 minutes. The reaction product was isolated and digested with the EcoRI restriction enzyme. The EcoRI fragment, thus obtained, was ligated with EcoRI-digested pUC18 vector. The obtained recombinant DNAs were designated pUC3–6 and pUC3–5. In pUC3–6, the levodione reductase gene was inserted in the opposite direction to the lac promoter of pUC18. In pUC3–5, the levodione reductase gene was inserted in the same direction as that of the lac promoter of pUC18.

(2) Expression of the Levodione Reductase Gene in *E. coli*

The recombinant DNAs pUC3–5 and pUC3–6 were used to transform *E. coli* JM109. The transformants thus obtained, *E. coli* JM109/pUC3–5 and *E. coli* JM109/pUC3–6, were cultivated in 3 ml of LB medium supplemented with 50 µg/ml of ampicillin. Ten µl of the above culture were inoculated into 10 ml of the same medium as above and incubated overnight at 37° C. From this culture, 5 ml of the cultured broth was centrifuged to separate the cells. With these procedures, the sample cells of *E. coli* JM109/pUC3–5 and *E. coli* JM109/pUC3–6 were prepared.

A reaction mixture (1 ml), (concentration of the components below are written as final concentration) consisting of the cells, 100 mM potassium phosphate buffer (pH 7.0), 0.6 mg/ml NAD$^+$ (Oriental Yeast), 31.2 unit/ml glucose dehydrogenase (Amano Pharmaceuticals), 5% (w/v) D-glucose, and 0.5% (w/v) levodione, was shaken at 30° C. for 24 hours. After the reaction, the reaction mixture was extracted with 1 ml of ethylacetate, and concentrated. The extract was analyzed by, gas chromatography (column: HR-20M (Shinwa Chemical Industries) 0.25 mmφ×30 m, column temperature: 160° C. (constant), injector temperature : 250° C., carrier gas: He (ca. 1 ml/min)). The yield and the optical purity of the product are summarized in Table 10.

TABLE 10

Production of actinol from levodione

| Strain | Conversion Yield (%) | Optical Purity (% e.e. for actinol) |
|---|---|---|
| *E. coli* JM109/pUC3-5 | 67.6 | 34.5 |
| *E. coli* JM109/pUC3-6 | 22.7 | 85 |

In addition, the reaction described above was carried out using cells of *E. coli* JM109/pUC3–5 and *E. coli* JM109/pUC3–6 prepared using M9 medium supplemented with casamino acids. The results are shown in Table 11.

TABLE 11

Production of actinol from levodione

| Strain | Conversion Yield (%) | Optical Purity (% e.e. for actinol) |
|---|---|---|
| *E. coli* JM109/pUC3-5 | 28 | 88.1 |
| *E. coli* JM109/pUC3-6 | 31.7 | 87.6 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for producing actinol comprising:
   (a) contacting levodione with a microorganism in a suitable medium, wherein the microorganism produces a polypeptide having levodione reductase activity and is transformed or transfected with a polynucleotide having the sequence of SEQ ID NO:2 or a polynucleotide that hybridizes to the complement of SEQ ID NO:2 under high stringency hybridizing conditions (6×SSC; 75° C.; overnight; washing two times in 6×SSC at 37° C.).

2. A process according to claim 1 wherein the polynucleotide has the sequence of SEQ ID NO:2 or a fragment of SEQ ID NO:2 which encodes a polypeptide having levodione reductase activity.

3. A process according to claim 1 wherein the polynucleotide encodes a polypeptide having the sequence of SEQ ID NO:1 or a fragment of SEQ ID NO:1 which has levodione reductase activity.

4. A process according to claim 2 wherein the polynucleotide has the sequence of SEQ ID NO:2.

5. A process according to claim 3 wherein the polynucleotide encodes a polypeptide having the sequence of SEQ ID NQ:1.

6. A process according to claim 1 wherein the polynucleotide encodes a polypepticle that has the following properties:
   a) catalyzes regio- and stereoselective reduction of levodione to actinol;
   b) a relative molecular mass of 142,000–155,000±10,000 Da consisting of four homologous subunits having a molecular mass of 36,000±5,000 Da each;
   c) a temperature optimum of 15–200° C. at pH 7.0;
   d) a pH optimum of 7.5; and
   e) requires NAD$^+$or NADH as a cofactor and is activated by monovalent cations selected from the group consisting of K$^+$, Na$^+$, Cs$^+$, Rb$^+$, and NH$_4^+$.

7. A process according to claim 1 wherein the polynucleotide is carded on a vector or plasmid.

8. A process according to claim 1 wherein the microorganism is a member of the genera selected from the group consisting of Cellulomonas, Corynebacterium, Planococcus, and Arthrobracter.

9. A process according to claim 1 further comprising isolating actinol from the medium.

* * * * *

UNITED STATES PATENT AND TRADEMARK OFFICE
CERTIFICATE OF CORRECTION

PATENT NO.     : 6,673,583 B2
DATED          : January 6, 2004
INVENTOR(S)    : Sakayu Shimizu and Masaru Wada It is certified that error appears in the above-identified patent and that said Letters Patent is hereby corrected as shown below:

Column 19,
Line 44, please change "NQ" to -- NO --;

Column 20,
Line 21, please change "polypepticle" to -- polypeptide --;
Line 29, please change "200°" to -- 20° --;
Line 35, please change "carded" to -- carried --;
Line 38, please italicize "*Cellulomonas, Corynebacterium, Planococcus,*";
Line 39, please change "Arthrobracter" to -- Arthrobacter --.

Signed and Sealed this

Twenty-second Day of June, 2004

JON W. DUDAS
*Acting Director of the United States Patent and Trademark Office*

SEQUENCE LISTING

<160> NUMBER OF SEQ ID NOS: 2
<210> SEQ ID NO 1
<211> LENGTH: 267
<212> TYPE: PRT
<213> ORGANISM: Corynebacterium aquaticum

<400> SEQUENCE: 1

```
Met Thr Ala Thr Ser Ser Pro Thr Thr Arg Phe Thr Asp Arg Val Val
  1               5                  10                  15

Leu Ile Thr Gly Gly Ser Gly Leu Gly Arg Ala Thr Ala Val Arg
             20                  25                  30

Leu Ala Ala Glu Gly Ala Lys Leu Ser Leu Val Asp Val Ser Ser Glu
             35                  40                  45

Gly Leu Glu Ala Ser Lys Ala Ala Val Leu Glu Thr Ala Pro Asp Ala
         50                  55                  60

Glu Val Leu Thr Thr Val Ala Asp Val Ser Asp Ala Gln Val Glu
 65                  70                  75                  80

Ala Tyr Val Thr Ala Thr Thr Glu Arg Phe Gly Arg Ile Asp Gly Phe
                 85                  90                  95

Phe Asn Asn Ala Gly Ile Glu Gly Lys Gln Asn Pro Thr Glu Ser Phe
             100                 105                 110

Thr Ala Ala Glu Phe Asp Lys Val Val Ser Ile Asn Leu Arg Gly Val
             115                 120                 125

Phe Leu Gly Leu Glu Lys Val Leu Lys Ile Met Arg Glu Gln Gly Ser
130                 135                 140

Gly Met Val Val Asn Thr Ala Ser Val Gly Ile Arg Gly Ile Gly
145                 150                 155                 160

Asn Gln Ser Gly Tyr Ala Ala Ala Lys His Gly Val Val Gly Leu Thr
                 165                 170                 175

Arg Asn Ser Ala Val Glu Tyr Gly Arg Tyr Gly Ile Arg Ile Asn Ala
             180                 185                 190

Ile Ala Pro Gly Ala Ile Trp Thr Pro Met Val Glu Asn Ser Met Lys
             195                 200                 205

Gln Leu Asp Pro Glu Asn Pro Arg Lys Ala Ala Glu Glu Phe Ile Gln
210                 215                 220

Val Asn Pro Ser Lys Arg Tyr Gly Glu Ala Pro Glu Ile Ala Ala Val
225                 230                 235                 240

Val Ala Phe Leu Leu Ser Asp Asp Ala Ser Tyr Val Asn Ala Thr Val
                 245                 250                 255

Val Pro Ile Asp Gly Gly Gln Ser Ala Ala Tyr
             260                 265
```

<210> SEQ ID NO 2
<211> LENGTH: 804
<212> TYPE: DNA
<213> ORGANISM: Corynebacterium aquaticum

<400> SEQUENCE: 2

```
atgaccgcaa ccagctcccc cacgacccgc ttcaccgacc gcgtcgtgct catcaccggc    60
ggcggctccg gcctcggccg tgcgaccgcc gtccgtctcg ccgccgaggg cgcgaagctc   120
tccctcgtcg acgtctcctc cgagggactc gaggcctcga aggccgccgt gctcgagacc   180
gcccccgacg ccgaggtcct caccaccgtc gccgacgtct cggacgaggc ccaggtcgag   240
gcctacgtca ccgccaccac cgagcgcttc ggccgcatcg acggcttctt caacaacgcc   300
```

```
ggcatcgagg gcaagcagaa cccgaccgag tcgttcaccg ccgccgagtt cgacaaggtc      360
gtctcgatca acctgcgcgg cgtgttcctc ggcctcgaga aggtcctgaa gatcatgcgc      420
gagcagggct ccggcatggt cgtcaacacg gcgagcgtcg gcggcatccg cggcatcggc      480
aaccagtccg gctacgccgc cgccaagcac ggggtcgtcg gtctcacccg caactccgcc      540
gtcgagtacg gccgctacgg catccgcatc aacgccatcg cccccggcgc catctggacg      600
ccgatggtcg agaactcgat gaagcagctc gacccggaga acccccgcaa ggccgccgag      660
gagttcatcc aggtcaaccc ctccaagcgc tacgcgagg cgcccgagat cgccgcggtc       720
gtcgccttcc tgctgtccga cgacgcctcg tacgtcaacg ccacggtcgt cccgatcgac      780
ggcgggcagt ccgccgcgta ctga                                             804
```